United States Patent
Aguilar et al.

(10) Patent No.: US 10,450,349 B2
(45) Date of Patent: Oct. 22, 2019

(54) MULTIVALENT FIBRONECTIN-INTEGRIN BINDING COMPOSITIONS AND METHODS OF USE THEREOF

(71) Applicant: Purdue Research Foundation, West Lafayette, IN (US)

(72) Inventors: Ruben Claudio Aguilar, West Lafayette, IN (US); Timothy L. Ratliff, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 60 days.

(21) Appl. No.: 15/448,772

(22) Filed: Mar. 3, 2017

(65) Prior Publication Data
US 2017/0252459 A1    Sep. 7, 2017

Related U.S. Application Data

(60) Provisional application No. 62/303,727, filed on Mar. 4, 2016.

(51) Int. Cl.
| | |
|---|---|
| *C07K 14/00* | (2006.01) |
| *A61K 45/06* | (2006.01) |
| *A61K 9/127* | (2006.01) |
| *C07K 14/705* | (2006.01) |
| *C07K 14/78* | (2006.01) |
| *A61K 47/62* | (2017.01) |
| *G01N 33/48* | (2006.01) |
| *G01N 33/68* | (2006.01) |
| *G01N 33/84* | (2006.01) |

(52) U.S. Cl.
CPC ............ *C07K 14/00* (2013.01); *A61K 9/1271* (2013.01); *A61K 45/06* (2013.01); *A61K 47/62* (2017.08); *C07K 14/70546* (2013.01); *C07K 14/78* (2013.01); *G01N 33/48* (2013.01); *G01N 33/6893* (2013.01); *G01N 33/84* (2013.01)

(58) Field of Classification Search
IPC .................................. A61K 47/62; C07K 14/00
See application file for complete search history.

(56) References Cited

U.S. PATENT DOCUMENTS

| | | |
|---|---|---|
| 6,638,518 B1 | 10/2003 | Ratliff |
| 6,676,945 B2 | 1/2004 | Laqueyrerie |
| 8,211,432 B2 | 7/2012 | Hook |
| 8,420,087 B2 | 4/2013 | Gallies |

OTHER PUBLICATIONS

James, Radiotherapy with or without Chemotherapy in Muscle-Invasive Bladder Cancer, N Engl J Med 2012;366:1477-88.*
Zhao, Characterization of the Fibronectin Binding Motif for a Unique Mycobacterial Fibronectin Attachment Protein, FAP, JBC 1999, vol. 274, No. 8 (Year: 1999).*
Celano (Cytotoxic effects of Gemcitabine-loaded liposomes in human anaplastic thyroid carcinoma cells, BMC Cancer 2004, 4:63 (Year: 2004).*
Zhao (Characterization of the Fibronectin Binding Motif for a Unique Mycobacterial Fibronectin Attachment Protein, FAP, JBC 1999, vol. 274, No. 8, of record) (Year: 1999).*
Celano (Cytotoxic effects of Gemcitabine-loaded liposomes in human anaplastic thyroid carcinoma cells, BMC Cancer 2004, 4:63, of record) (Year: 2004).*
Chelius (Capture of Peptides with N-Terminal Serine and Threonine: A Sequence-Specific Chemical Method for Peptide Mixture Simplification, Bioconjugate Chem. 2003, 14: 205-211) (Year: 2003).*
Coon, B.G., "Fibronectin attachment protein from bacillus Calmette-Guerin as targeting agent for bladder tumor cells." Int. J. Cancer: 131,591-600 (2012).
Berrade, L., "Expressed protein ligation: a resourceful tool to study protein structure and function." Cell. Mol. Life Sci. (2009) 66:3909-3922.
Ruoslahti, E. "New perspectives in cell adhesion: RGD and Integrins." Science, 238(4826), 491-497 (1987).

* cited by examiner

*Primary Examiner* — Karlheinz R. Skowronek
*Assistant Examiner* — Khalid Kader
(74) *Attorney, Agent, or Firm* — Purdue Research Foundation; Liang Zeng Yan

(57) ABSTRACT

The invention provides multivalent fibronectin-integrin binding compositions and methods of use thereof. In certain embodiments, the invention provides peptide compositions that include at least two fibronectin binding peptides coupled together as a cancer therapeutic or a diagnostic tool.

14 Claims, 1 Drawing Sheet
Specification includes a Sequence Listing.

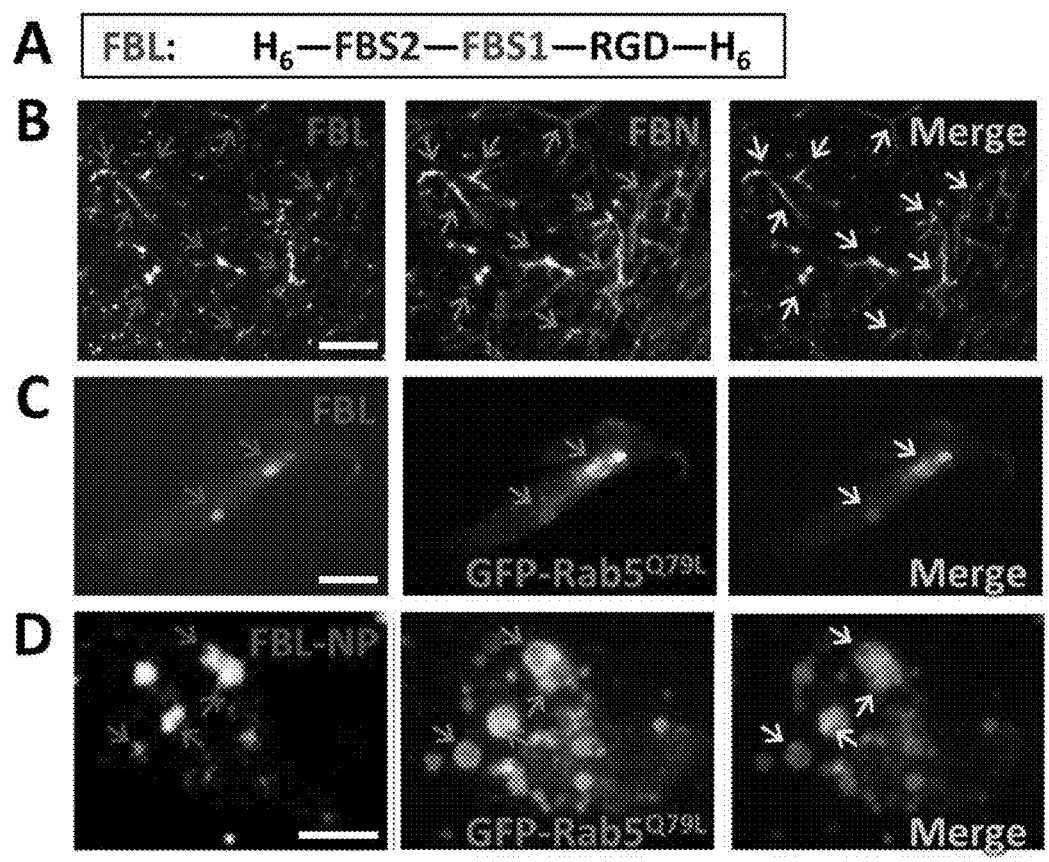

SEQUENCE LISTING

```
<160> NUMBER OF SEQ ID NOS: 41

<210> SEQ ID NO 1
<211> LENGTH: 79
<212> TYPE: PRT
<213> ORGANISM: artificial sequence
<220> FEATURE:
<223> OTHER INFORMATION: fibronectin binding peptide

<400> SEQUENCE: 1

Met Gly Ser Ser His His His His His His Ser Ser Gly Asn Arg Gln
1               5                   10                  15

Arg Trp Phe Val Val Trp Leu Ser Thr Gly Gly Asn Asp Thr Arg Ile
            20                  25                  30

Val Leu Gly Arg Leu Asp Gln Leu Val Pro Arg Gly Ser His Met Ala
        35                  40                  45

Ser Met Thr Gly Gly Gln Gln Met Gly Arg Gly Asp Phe Arg Ser Ser
    50                  55                  60

Val Asp Lys Leu Ala Ala Ala Leu Glu His His His His His
65                  70                  75

<210> SEQ ID NO 2
<211> LENGTH: 79
<212> TYPE: PRT
<213> ORGANISM: artificial sequence
<220> FEATURE:
<223> OTHER INFORMATION: fibronectin binding peptide

<400> SEQUENCE: 2

Met Gly Ser Ser His His His His His His Ser Ser Gly Asn Arg Gln
```

```
                1               5                   10                  15
            Arg Ile Val Leu Gly Arg Leu Ser Thr Gly Gly Asn Asp Thr Arg Trp
                            20                  25                  30

Phe Val Val Trp Leu Asp Gln Leu Val Pro Arg Gly Ser His Met Ala
                            35                  40                  45

Ser Met Thr Gly Gly Gln Gln Met Gly Arg Gly Asp Phe Arg Ser Ser
                        50                  55                  60

Val Asp Lys Leu Ala Ala Ala Leu Glu His His His His His
            65                  70                  75
```

<210> SEQ ID NO 3
<211> LENGTH: 79
<212> TYPE: PRT
<213> ORGANISM: artificial sequence
<220> FEATURE:
<223> OTHER INFORMATION: fibronectin binding peptide

<400> SEQUENCE: 3

```
            Met Gly Ser Ser His His His His His His Ser Ser Gly Asn Arg Gln
            1               5                   10                  15

Arg Ile Val Leu Gly Arg Leu Ser Thr Gly Gly Asn Asp Thr Arg Ile
                            20                  25                  30

Val Leu Gly Arg Leu Asp Gln Leu Val Pro Arg Gly Ser His Met Ala
                            35                  40                  45

Ser Met Thr Gly Gly Gln Gln Met Gly Arg Gly Asp Phe Arg Ser Ser
                        50                  55                  60

Val Asp Lys Leu Ala Ala Ala Leu Glu His His His His His
            65                  70                  75
```

<210> SEQ ID NO 4
<211> LENGTH: 79
<212> TYPE: PRT
<213> ORGANISM: artificial sequence
<220> FEATURE:
<223> OTHER INFORMATION: fibronectin binding peptide

<400> SEQUENCE: 4

```
            Met Gly Ser Ser His His His His His His Ser Ser Gly Asn Arg Gln
            1               5                   10                  15

Arg Trp Phe Val Val Trp Leu Ser Thr Gly Gly Asn Asp Thr Arg Trp
                            20                  25                  30

Phe Val Val Trp Leu Asp Gln Leu Val Pro Arg Gly Ser His Met Ala
                            35                  40                  45

Ser Met Thr Gly Gly Gln Gln Met Gly Arg Gly Asp Phe Arg Ser Ser
                        50                  55                  60

Val Asp Lys Leu Ala Ala Ala Leu Glu His His His His His
            65                  70                  75
```

<210> SEQ ID NO 5
<211> LENGTH: 55
<212> TYPE: PRT
<213> ORGANISM: artificial sequence
<220> FEATURE:
<223> OTHER INFORMATION: fibronectin binding peptide

<400> SEQUENCE: 5

```
            Met Arg Lys Gln Arg Trp Phe Val Val Trp Leu Gly Glu Phe Gly Phe
            1               5                   10                  15

Glu Trp Tyr Tyr Gln Gly Pro Gly Tyr Asp Gln Gln Gly Tyr Asp Gln
                            20                  25                  30
```

Gln Gly Leu Glu Asp Leu Arg Pro Lys Ser Ser Leu Gln Gly Ile Gly
        35                  40                  45

Thr His His His His His
    50                  55

<210> SEQ ID NO 6
<211> LENGTH: 73
<212> TYPE: PRT
<213> ORGANISM: artificial sequence
<220> FEATURE:
<223> OTHER INFORMATION: fibronectin binding peptide

<400> SEQUENCE: 6

Met Gly Ser Ser His His His His His His Ser Ser Gly Asn Arg Gln
1               5                   10                  15

Arg Trp Phe Val Val Trp Leu Ser Thr Gly Gly Asn Asp Thr Arg Ile
            20                  25                  30

Val Leu Gly Arg Leu Asp Gln Leu Val Pro Arg Gly Ser His Met Ala
        35                  40                  45

Ser Met Thr Gly Gly Gln Gln Met Gly Arg Gly Asp Phe Arg Ser Ser
    50                  55                  60

Val Asp Lys Leu Ala Ala Ala Leu Glu
65                  70

<210> SEQ ID NO 7
<211> LENGTH: 73
<212> TYPE: PRT
<213> ORGANISM: artificial sequence
<220> FEATURE:
<223> OTHER INFORMATION: fibronectin binding peptide

<400> SEQUENCE: 7

Met Gly Ser Ser His His His His His His Ser Ser Gly Asn Arg Gln
1               5                   10                  15

Arg Ile Val Leu Gly Arg Leu Ser Thr Gly Gly Asn Asp Thr Arg Trp
            20                  25                  30

Phe Val Val Trp Leu Asp Gln Leu Val Pro Arg Gly Ser His Met Ala
        35                  40                  45

Ser Met Thr Gly Gly Gln Gln Met Gly Arg Gly Asp Phe Arg Ser Ser
    50                  55                  60

Val Asp Lys Leu Ala Ala Ala Leu Glu
65                  70

<210> SEQ ID NO 8
<211> LENGTH: 73
<212> TYPE: PRT
<213> ORGANISM: artificial sequence
<220> FEATURE:
<223> OTHER INFORMATION: fibronectin binding peptide

<400> SEQUENCE: 8

Met Gly Ser Ser His His His His His His Ser Ser Gly Asn Arg Gln
1               5                   10                  15

Arg Ile Val Leu Gly Arg Leu Ser Thr Gly Gly Asn Asp Thr Arg Ile
            20                  25                  30

Val Leu Gly Arg Leu Asp Gln Leu Val Pro Arg Gly Ser His Met Ala
        35                  40                  45

Ser Met Thr Gly Gly Gln Gln Met Gly Arg Gly Asp Phe Arg Ser Ser
    50                  55                  60

Val Asp Lys Leu Ala Ala Ala Leu Glu
65              70

<210> SEQ ID NO 9
<211> LENGTH: 73
<212> TYPE: PRT
<213> ORGANISM: artificial sequence
<220> FEATURE:
<223> OTHER INFORMATION: fibronectin binding peptide

<400> SEQUENCE: 9

Met Gly Ser Ser His His His His His His Ser Ser Gly Asn Arg Gln
1               5                   10                  15

Arg Trp Phe Val Val Trp Leu Ser Thr Gly Gly Asn Asp Thr Arg Trp
            20                  25                  30

Phe Val Val Trp Leu Asp Gln Leu Val Pro Arg Gly Ser His Met Ala
        35                  40                  45

Ser Met Thr Gly Gly Gln Gln Met Gly Arg Gly Asp Phe Arg Ser Ser
    50                  55                  60

Val Asp Lys Leu Ala Ala Ala Leu Glu
65              70

<210> SEQ ID NO 10
<211> LENGTH: 49
<212> TYPE: PRT
<213> ORGANISM: artificial sequence
<220> FEATURE:
<223> OTHER INFORMATION: fibronectin binding peptide

<400> SEQUENCE: 10

Met Arg Lys Gln Arg Trp Phe Val Val Trp Leu Gly Glu Phe Gly Phe
1               5                   10                  15

Glu Trp Tyr Tyr Gln Gly Pro Gly Tyr Asp Gln Gln Gly Tyr Asp Gln
            20                  25                  30

Gln Gly Leu Glu Asp Leu Arg Pro Lys Ser Ser Leu Gln Gly Ile Gly
        35                  40                  45

Thr

<210> SEQ ID NO 11
<211> LENGTH: 69
<212> TYPE: PRT
<213> ORGANISM: artificial sequence
<220> FEATURE:
<223> OTHER INFORMATION: fibronectin binding peptide

<400> SEQUENCE: 11

Ser Ser Gly Asn Arg Gln Arg Trp Phe Val Val Trp Leu Ser Thr Gly
1               5                   10                  15

Gly Asn Asp Thr Arg Ile Val Leu Gly Arg Leu Asp Gln Leu Val Pro
            20                  25                  30

Arg Gly Ser His Met Ala Ser Met Thr Gly Gly Gln Gln Met Gly Arg
        35                  40                  45

Gly Asp Phe Arg Ser Ser Val Asp Lys Leu Ala Ala Ala Leu Glu His
    50                  55                  60

His His His His
65

<210> SEQ ID NO 12
<211> LENGTH: 69
<212> TYPE: PRT
<213> ORGANISM: artificial sequence
<220> FEATURE:
<223> OTHER INFORMATION: fibronectin binding peptide

<400> SEQUENCE: 12

Ser Ser Gly Asn Arg Gln Arg Ile Val Leu Gly Arg Leu Ser Thr Gly
1               5                   10                  15

Gly Asn Asp Thr Arg Trp Phe Val Val Trp Leu Asp Gln Leu Val Pro
            20                  25                  30

Arg Gly Ser His Met Ala Ser Met Thr Gly Gly Gln Gln Met Gly Arg
        35                  40                  45

Gly Asp Phe Arg Ser Ser Val Asp Lys Leu Ala Ala Ala Leu Glu His
    50                  55                  60

His His His His His
65

<210> SEQ ID NO 13
<211> LENGTH: 69
<212> TYPE: PRT
<213> ORGANISM: artificial sequence
<220> FEATURE:
<223> OTHER INFORMATION: fibronectin binding peptide

<400> SEQUENCE: 13

Ser Ser Gly Asn Arg Gln Arg Ile Val Leu Gly Arg Leu Ser Thr Gly
1               5                   10                  15

Gly Asn Asp Thr Arg Ile Val Leu Gly Arg Leu Asp Gln Leu Val Pro
            20                  25                  30

Arg Gly Ser His Met Ala Ser Met Thr Gly Gly Gln Gln Met Gly Arg
        35                  40                  45

Gly Asp Phe Arg Ser Ser Val Asp Lys Leu Ala Ala Ala Leu Glu His
    50                  55                  60

His His His His His
65

<210> SEQ ID NO 14
<211> LENGTH: 69
<212> TYPE: PRT
<213> ORGANISM: artificial sequence
<220> FEATURE:
<223> OTHER INFORMATION: fibronectin binding peptide

<400> SEQUENCE: 14

Ser Ser Gly Asn Arg Gln Arg Trp Phe Val Val Trp Leu Ser Thr Gly
1               5                   10                  15

Gly Asn Asp Thr Arg Trp Phe Val Val Trp Leu Asp Gln Leu Val Pro
            20                  25                  30

Arg Gly Ser His Met Ala Ser Met Thr Gly Gly Gln Gln Met Gly Arg
        35                  40                  45

Gly Asp Phe Arg Ser Ser Val Asp Lys Leu Ala Ala Ala Leu Glu His
    50                  55                  60

His His His His His
65

<210> SEQ ID NO 15
<211> LENGTH: 63
<212> TYPE: PRT
<213> ORGANISM: artificial sequence
<220> FEATURE:
<223> OTHER INFORMATION: fibronectin binding peptide

<400> SEQUENCE: 15

Ser Ser Gly Asn Arg Gln Arg Trp Phe Val Val Trp Leu Ser Thr Gly
1               5                   10                  15

Gly Asn Asp Thr Arg Ile Val Leu Gly Arg Leu Asp Gln Leu Val Pro
                20                  25                  30

Arg Gly Ser His Met Ala Ser Met Thr Gly Gly Gln Gln Met Gly Arg
            35                  40                  45

Gly Asp Phe Arg Ser Ser Val Asp Lys Leu Ala Ala Ala Leu Glu
        50                  55                  60

<210> SEQ ID NO 16
<211> LENGTH: 63
<212> TYPE: PRT
<213> ORGANISM: artificial sequence
<220> FEATURE:
<223> OTHER INFORMATION: fibronectin binding peptide

<400> SEQUENCE: 16

Ser Ser Gly Asn Arg Gln Arg Ile Val Leu Gly Arg Leu Ser Thr Gly
1               5                   10                  15

Gly Asn Asp Thr Arg Trp Phe Val Val Trp Leu Asp Gln Leu Val Pro
                20                  25                  30

Arg Gly Ser His Met Ala Ser Met Thr Gly Gly Gln Gln Met Gly Arg
            35                  40                  45

Gly Asp Phe Arg Ser Ser Val Asp Lys Leu Ala Ala Ala Leu Glu
        50                  55                  60

<210> SEQ ID NO 17
<211> LENGTH: 63
<212> TYPE: PRT
<213> ORGANISM: artificial sequence
<220> FEATURE:
<223> OTHER INFORMATION: fibronectin binding peptide

<400> SEQUENCE: 17

Ser Ser Gly Asn Arg Gln Arg Ile Val Leu Gly Arg Leu Ser Thr Gly
1               5                   10                  15

Gly Asn Asp Thr Arg Ile Val Leu Gly Arg Leu Asp Gln Leu Val Pro
                20                  25                  30

Arg Gly Ser His Met Ala Ser Met Thr Gly Gly Gln Gln Met Gly Arg
            35                  40                  45

Gly Asp Phe Arg Ser Ser Val Asp Lys Leu Ala Ala Ala Leu Glu
        50                  55                  60

<210> SEQ ID NO 18
<211> LENGTH: 63
<212> TYPE: PRT
<213> ORGANISM: artificial sequence
<220> FEATURE:
<223> OTHER INFORMATION: fibronectin binding peptide

<400> SEQUENCE: 18

Ser Ser Gly Asn Arg Gln Arg Trp Phe Val Val Trp Leu Ser Thr Gly
1               5                   10                  15

Gly Asn Asp Thr Arg Trp Phe Val Val Trp Leu Asp Gln Leu Val Pro
                20                  25                  30

Arg Gly Ser His Met Ala Ser Met Thr Gly Gly Gln Gln Met Gly Arg
            35                  40                  45

Gly Asp Phe Arg Ser Ser Val Asp Lys Leu Ala Ala Ala Leu Glu
        50                  55                  60

```
<210> SEQ ID NO 19
<211> LENGTH: 49
<212> TYPE: PRT
<213> ORGANISM: artificial sequence
<220> FEATURE:
<223> OTHER INFORMATION: fibronectin binding peptide

<400> SEQUENCE: 19

Met Arg Lys Gln Arg Trp Phe Val Val Trp Leu Gly Glu Phe Gly Phe
1               5                   10                  15

Glu Trp Tyr Tyr Gln Gly Pro Gly Tyr Asp Gln Gln Gly Tyr Asp Gln
            20                  25                  30

Gln Gly Leu Glu Asp Leu Arg Pro Lys Ser Ser Leu Gly Ile Gly
        35                  40                  45

Thr

<210> SEQ ID NO 20
<211> LENGTH: 47
<212> TYPE: PRT
<213> ORGANISM: artificial sequence
<220> FEATURE:
<223> OTHER INFORMATION: fibronectin binding peptide

<400> SEQUENCE: 20

Ser Ser Gly Asn Arg Gln Arg Trp Phe Val Val Trp Leu Ser Thr Gly
1               5                   10                  15

Gly Asn Asp Thr Arg Ile Val Leu Gly Arg Leu Asp Gln Leu Val Pro
            20                  25                  30

Arg Gly Ser His Met Ala Ser Met Thr Gly Gly Gln Gln Met Gly
        35                  40                  45

<210> SEQ ID NO 21
<211> LENGTH: 47
<212> TYPE: PRT
<213> ORGANISM: artificial sequence
<220> FEATURE:
<223> OTHER INFORMATION: fibronectin binding peptide

<400> SEQUENCE: 21

Ser Ser Gly Asn Arg Gln Arg Ile Val Leu Gly Arg Leu Ser Thr Gly
1               5                   10                  15

Gly Asn Asp Thr Arg Trp Phe Val Val Trp Leu Asp Gln Leu Val Pro
            20                  25                  30

Arg Gly Ser His Met Ala Ser Met Thr Gly Gly Gln Gln Met Gly
        35                  40                  45

<210> SEQ ID NO 22
<211> LENGTH: 47
<212> TYPE: PRT
<213> ORGANISM: artificial sequence
<220> FEATURE:
<223> OTHER INFORMATION: fibronectin binding peptide

<400> SEQUENCE: 22

Ser Ser Gly Asn Arg Gln Arg Ile Val Leu Gly Arg Leu Ser Thr Gly
1               5                   10                  15

Gly Asn Asp Thr Arg Ile Val Leu Gly Arg Leu Asp Gln Leu Val Pro
            20                  25                  30

Arg Gly Ser His Met Ala Ser Met Thr Gly Gly Gln Gln Met Gly
        35                  40                  45
```

```
<210> SEQ ID NO 23
<211> LENGTH: 47
<212> TYPE: PRT
<213> ORGANISM: artificial sequence
<220> FEATURE:
<223> OTHER INFORMATION: fibronectin binding peptide

<400> SEQUENCE: 23

Ser Ser Gly Asn Arg Gln Arg Trp Phe Val Val Trp Leu Ser Thr Gly
1               5                   10                  15

Gly Asn Asp Thr Arg Trp Phe Val Val Trp Leu Asp Gln Leu Val Pro
            20                  25                  30

Arg Gly Ser His Met Ala Ser Met Thr Gly Gly Gln Gln Met Gly
        35                  40                  45

<210> SEQ ID NO 24
<211> LENGTH: 26
<212> TYPE: PRT
<213> ORGANISM: artificial sequence
<220> FEATURE:
<223> OTHER INFORMATION: fibronectin binding peptide

<400> SEQUENCE: 24

Ser Ser Gly Asn Arg Gln Arg Trp Phe Val Val Trp Leu Ser Thr Gly
1               5                   10                  15

Gly Asn Asp Thr Arg Ile Val Leu Gly Arg
            20                  25

<210> SEQ ID NO 25
<211> LENGTH: 26
<212> TYPE: PRT
<213> ORGANISM: artificial sequence
<220> FEATURE:
<223> OTHER INFORMATION: fibronectin binding peptide

<400> SEQUENCE: 25

Ser Ser Gly Asn Arg Gln Arg Ile Val Leu Gly Arg Leu Ser Thr Gly
1               5                   10                  15

Gly Asn Asp Thr Arg Trp Phe Val Val Trp
            20                  25

<210> SEQ ID NO 26
<211> LENGTH: 26
<212> TYPE: PRT
<213> ORGANISM: artificial sequence
<220> FEATURE:
<223> OTHER INFORMATION: fibronectin binding peptide

<400> SEQUENCE: 26

Ser Ser Gly Asn Arg Gln Arg Ile Val Leu Gly Arg Leu Ser Thr Gly
1               5                   10                  15

Gly Asn Asp Thr Arg Ile Val Leu Gly Arg
            20                  25

<210> SEQ ID NO 27
<211> LENGTH: 26
<212> TYPE: PRT
<213> ORGANISM: artificial sequence
<220> FEATURE:
<223> OTHER INFORMATION: fibronectin binding peptide

<400> SEQUENCE: 27

Ser Ser Gly Asn Arg Gln Arg Trp Phe Val Val Trp Leu Ser Thr Gly
1               5                   10                  15
```

Gly Asn Asp Thr Arg Trp Phe Val Val Trp
            20                  25

<210> SEQ ID NO 28
<211> LENGTH: 41
<212> TYPE: PRT
<213> ORGANISM: artificial sequence
<220> FEATURE:
<223> OTHER INFORMATION: fibronectin binding peptide

<400> SEQUENCE: 28

Arg Trp Phe Val Val Trp Leu Ser Thr Gly Gly Asn Asp Thr Arg Ile
1               5                   10                  15

Val Leu Gly Arg Leu Asp Gln Leu Val Pro Arg Gly Ser His Met Ala
            20                  25                  30

Ser Met Thr Gly Gly Gln Gln Met Gly
        35                  40

<210> SEQ ID NO 29
<211> LENGTH: 41
<212> TYPE: PRT
<213> ORGANISM: artificial sequence
<220> FEATURE:
<223> OTHER INFORMATION: fibronectin binding peptide

<400> SEQUENCE: 29

Arg Ile Val Leu Gly Arg Leu Ser Thr Gly Gly Asn Asp Thr Arg Trp
1               5                   10                  15

Phe Val Val Trp Leu Asp Gln Leu Val Pro Arg Gly Ser His Met Ala
            20                  25                  30

Ser Met Thr Gly Gly Gln Gln Met Gly
        35                  40

<210> SEQ ID NO 30
<211> LENGTH: 41
<212> TYPE: PRT
<213> ORGANISM: artificial sequence
<220> FEATURE:
<223> OTHER INFORMATION: fibronectin binding peptide

<400> SEQUENCE: 30

Arg Ile Val Leu Gly Arg Leu Ser Thr Gly Gly Asn Asp Thr Arg Ile
1               5                   10                  15

Val Leu Gly Arg Leu Asp Gln Leu Val Pro Arg Gly Ser His Met Ala
            20                  25                  30

Ser Met Thr Gly Gly Gln Gln Met Gly
        35                  40

<210> SEQ ID NO 31
<211> LENGTH: 41
<212> TYPE: PRT
<213> ORGANISM: artificial sequence
<220> FEATURE:
<223> OTHER INFORMATION: fibronectin binding peptide

<400> SEQUENCE: 31

Arg Trp Phe Val Val Trp Leu Ser Thr Gly Gly Asn Asp Thr Arg Trp
1               5                   10                  15

Phe Val Val Trp Leu Asp Gln Leu Val Pro Arg Gly Ser His Met Ala
            20                  25                  30

Ser Met Thr Gly Gly Gln Gln Met Gly
        35                  40

```
<210> SEQ ID NO 32
<211> LENGTH: 20
<212> TYPE: PRT
<213> ORGANISM: artificial sequence
<220> FEATURE:
<223> OTHER INFORMATION: fibronectin binding peptide

<400> SEQUENCE: 32

Arg Trp Phe Val Val Trp Leu Ser Thr Gly Gly Asn Asp Thr Arg Ile
1               5                   10                  15

Val Leu Gly Arg
            20

<210> SEQ ID NO 33
<211> LENGTH: 20
<212> TYPE: PRT
<213> ORGANISM: artificial sequence
<220> FEATURE:
<223> OTHER INFORMATION: fibronectin binding peptide

<400> SEQUENCE: 33

Arg Ile Val Leu Gly Arg Leu Ser Thr Gly Gly Asn Asp Thr Arg Trp
1               5                   10                  15

Phe Val Val Trp
            20

<210> SEQ ID NO 34
<211> LENGTH: 20
<212> TYPE: PRT
<213> ORGANISM: artificial sequence
<220> FEATURE:
<223> OTHER INFORMATION: fibronecting binding peptide

<400> SEQUENCE: 34

Arg Ile Val Leu Gly Arg Leu Ser Thr Gly Gly Asn Asp Thr Arg Ile
1               5                   10                  15

Val Leu Gly Arg
            20

<210> SEQ ID NO 35
<211> LENGTH: 20
<212> TYPE: PRT
<213> ORGANISM: artificial sequence
<220> FEATURE:
<223> OTHER INFORMATION: fibronectin binding peptide

<400> SEQUENCE: 35

Arg Trp Phe Val Val Trp Leu Ser Thr Gly Gly Asn Asp Thr Arg Trp
1               5                   10                  15

Phe Val Val Trp
            20

<210> SEQ ID NO 36
<211> LENGTH: 14
<212> TYPE: PRT
<213> ORGANISM: artificial sequence
<220> FEATURE:
<223> OTHER INFORMATION: fibronectin binding peptide

<400> SEQUENCE: 36

Arg Ile Val Leu Gly Arg Leu Ser Thr Gly Gly Asn Asp Thr
1               5                   10

<210> SEQ ID NO 37
```

```
<211> LENGTH: 14
<212> TYPE: PRT
<213> ORGANISM: artificial sequence
<220> FEATURE:
<223> OTHER INFORMATION: fibronectin binding peptide

<400> SEQUENCE: 37

Leu Ser Thr Gly Gly Asn Asp Thr Arg Trp Phe Val Val Trp
1               5                   10

<210> SEQ ID NO 38
<211> LENGTH: 14
<212> TYPE: PRT
<213> ORGANISM: artificial sequence
<220> FEATURE:
<223> OTHER INFORMATION: fibronectin binding peptide

<400> SEQUENCE: 38

Arg Trp Phe Val Val Trp Leu Ser Thr Gly Gly Asn Asp Thr
1               5                   10

<210> SEQ ID NO 39
<211> LENGTH: 14
<212> TYPE: PRT
<213> ORGANISM: artificial sequence
<220> FEATURE:
<223> OTHER INFORMATION: fibronectin binding peptide

<400> SEQUENCE: 39

Leu Ser Thr Gly Gly Asn Asp Thr Arg Ile Val Leu Gly Arg
1               5                   10

<210> SEQ ID NO 40
<211> LENGTH: 6
<212> TYPE: PRT
<213> ORGANISM: artificial sequence
<220> FEATURE:
<223> OTHER INFORMATION: fibronectin binding peptide

<400> SEQUENCE: 40

Arg Trp Phe Val Val Trp
1               5

<210> SEQ ID NO 41
<211> LENGTH: 6
<212> TYPE: PRT
<213> ORGANISM: artificial sequence
<220> FEATURE:
<223> OTHER INFORMATION: fibronectin binding peptide

<400> SEQUENCE: 41

Arg Ile Val Leu Gly Arg
1               5
```

MULTIVALENT FIBRONECTIN-INTEGRIN BINDING COMPOSITIONS AND METHODS OF USE THEREOF

CROSS-REFERENCE TO RELATED APPLICATIONS

The present U.S. patent application is related to and claims the priority benefit of the U.S. Provisional Patent Application Ser. No. 62/303,727, filed Mar. 4, 2016, the contents of which are hereby incorporated by reference in their entirety into the present disclosure.

SEQUENCE LISTING

This application contains a Sequence Listing which has been submitted as sequence listing text file "66861_03_ST25.txt", file size 21 KB, created on Feb. 27, 2017. The aforementioned sequence listing is hereby incorporated by reference in its entirety.

BACKGROUND

This section introduces aspects that may help facilitate a better understanding of the disclosure. Accordingly, these statements are to be read in this light and are not to be understood as admissions about what is or is not prior art.

Bladder cancer is the 4th most prevalent cancer in men and the 11th in women. Despite its impact on human health, therapeutic approaches against this malignancy are limited. Under normal conditions, bladder epithelial cells assemble as a tightly sealed, non-permeable barrier bearing a thick layer of glycosaminoglycans (GAG) that greatly contributes to isolate the urothelium from the urine. However, upon carcinoma development, relatively undifferentiated tumor cells, less competent for secretion, become exposed while normal cells remain shielded by the GAG layer. Those uncovered tumor cells are suitable targets for cytotoxic agents. However, dilution of the bladder content by constant urine influx and periodical voiding constitute major challenges for therapeutic approaches with poor or non-existing cell binding/targeting.

Current adjuvant therapies for bladder cancer use live *Bacillus* Calmette-Guerin (BCG) to target bladder tumor cells and trigger an anti-tumor immune response. The ability of BCG to bind the exposed tumor cells via its fibronectin attachment protein (FAP) allows the bacterium to overcome the above mentioned problems (dilution by urine influx and elimination by bladder content voiding). However, this is not a primary anti-cancer therapy and quickly leads to patient hypersensitivity (usually producing abandonment of the treatment), morbidity and risk of infection. Purified proteins such as FAP and other ligands may provide targeting substitutes devoid of these undesirable secondary effects; however, as opposed to BCG, they are not multivalent and several of molecules are required to be tied together to induce a rate of uptake by tumor cells meaningful for patient treatment. See Coon, et al. (*Int. J. Cancer*, 2012, 131(3): 591-600).

BRIEF SUMMARY OF INVENTION

The invention provides artificial multivalent fibronectin/integrin targeting agents that lack the negative effects of live *Bacillus* Calmette-Guerin (BCG) described above. Furthermore, due to the multivalency of the claimed compositions, the compositions of the invention do not require multiple molecules to be tied together, i.e., microclustering is not required. In that manner, the compositions of the invention have improved effective binding affinity (avidity) and rate of uptake as compared to monovalent compositions that are tied together into a microcluster as well as superior protein solubility and stability as compared to microclustered compositions.

In certain embodiments, a peptide composition comprise a peptide of an amino acid sequence selected from the group consisting of SEQ ID NOs.: 1-41, a combination of any of those sequences, a substantial fragment thereof, or a pharmaceutically acceptable salt thereof. Compositions of the invention are not limited to two fibronectin binding peptide fragments and can include 3, 4, 5, 6, 7, 8, 9, 10, 15, 20, etc. copies of fibronectin binding peptides selected from the group consisting of SEQ ID NOs.: 1~41.

In certain embodiments, the peptide composition comprises a plurality of an amino acid sequence selected from the group consisting of SEQ ID NOs.: 1-41, a combination of any of those sequences, a substantial fragment thereof, or a pharmaceutically acceptable salt thereof.

In certain embodiments, the peptide composition further comprises a cytotoxic agent. In some preferred embodiments, the cytotoxic agent is an anti-cancer agent.

In certain embodiments, the peptide composition further comprises a pharmaceutically acceptable carrier. In some preferred embodiments, the pharmaceutically acceptable carrier is a liposome.

In certain embodiments, the peptide composition further comprises a label for identifying cancer cells wherein cancerous cells express a component that may be bound by fibronectin/integrin binding peptides, wherein the label is coupled to the peptide composition.

It is to be understood that a pharmaceutical composition disclosed herein may be combined with other components, including, but not limited to, other therapeutically active compounds by the same or different mode of action, and one or more pharmaceutically acceptable carriers, diluents, excipients, and the like.

In some other embodiments, it is appreciated herein that the compounds described herein may be used alone or in combination with other compounds useful for treating cancer, including those compounds that may be therapeutically effective by the same or different mode of action.

In some embodiments, this invention claims a method for targeting or identifying cancer cells wherein cancerous cells express a component that may be bound by fibronectin/integrin binding peptides, the method comprising the step of administering to a subject of a peptide composition comprising a peptide of an amino acid sequence selected from the group consisting of SEQ ID NOs.: 1-41, a combination of any of those sequences, or a substantial fragment thereof, wherein a tracing agent is coupled to the peptide composition.

In some embodiments, this invention claims a method for treating a cancer wherein cancerous cells express a component that may be bound by fibronectin/integrin binding peptides, the method comprising the step of administering to a patient of said cancer therapeutically effective amount of a peptide composition comprising a peptide of an amino acid sequence selected from the group consisting of SEQ ID NOs.: 1-41, a combination of any of those sequences, or a substantial fragment thereof, wherein an anti-cancer agent is coupled to the peptide composition. In some preferred embodiments, the invention is related to a method of treatment for a bladder cancer.

In some embodiments, disclosed herein is a method for treating a patient with cancer, the method comprising the step of administering a therapeutically effective amount of a pharmaceutical composition comprising a compound disclosed herein to the patient in need of relief from said cancer. It is to be understood that the composition may include other components, including, but not limited to, other therapeutically active compounds by the same or different mode of action, and one or more pharmaceutically acceptable carriers, diluents, excipients, and the like.

BRIEF DESCRIPTION OF THE FIGURES

FIG. 1, panels A-D, shows that compositions of the invention co-localize with Fibronectin (FBN) and it is internalized by human bladder cancer cells. Panel A illustrates an exemplary composition of the invention (Fibronectin/integrin binding Ligand: FBL). $H_6$ represents a His$_6$ tag, FBS1 and FBS2 are two different fibronectin binding sites (FBSs) taken from fibronectin attachment protein (FAP), and RGD represents tripeptide Arg-Gly-Asp. Panel B is a set of slides showing that compositions of the invention co-localize with FBN. T24 human bladder tumor cells grown on coverslips for 24 h were incubated with compositions of the invention, washed, fixed and immunostained with anti-His$_6$ (red) and anti-FBN (green) antibodies. Arrows point some areas of colocalization. Scale bar: 20 microns. Panel C is a set of slides showing internalization of compositions of the invention by cancer cells. T24 cells expressing GFP-tagged constitutively activated Rab5 (Q79L) mutant were grown on coverslips. This Rab5 variant leads to the formation of easy to visualize giant GFP-labeled endosomes. Therefore, composition signal located inside GFP-positive structures shows that the composition has been internalized by the tumor cells. T24 cells were incubated with the claimed compositions, fixed and immunostained with anti-His6 antibody. Arrows point to some to internalized compositions of the invention. Scale bar: 20 microns. Panel D is a set of slides showing nanoparticle uptake induced by compositions of the invention. GFP-Rab5Q79L expressing cells were incubated with fluorescent nanoparticles decorated with compositions of the invention. Internalized compositions of the invention were detected as fluorescent signal detected inside of GFP-labeled structures (Arrows). Scale bar: 10 microns.

DETAILED DESCRIPTION OF THE INVENTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The invention provides artificial multivalent fibronectin/integrin targeting agents that lack the negative effects of live *Bacillus* Calmette-Guerin (BCG) described above. Furthermore, due to the multivalency of the claimed compositions, the compositions of the invention do not require multiple molecules to be tied together, i.e., microclustering is not required. In that manner, the compositions of the invention have improved effective binding affinity (avidity) and rate of uptake as compared to monovalent compositions that are tied together into a microcluster as well as superior protein solubility and stability as compared to microclustered compositions.

The claimed compositions can be composed of one or more fibronectin binding peptides. Those peptides, for example, can come from *Mycobacterium bovis Bacillus* Calmette-Guerin (BCG) FAP or from other fibronectin binding proteins, as well as any derivative (including amino acid substitutions or additions, or post translational modifications, e.g. methylation, acylation, ubiquitination and the like) or substantial fragment thereof that is capable of binding to Integrin-bound fibronectin or free integrins and undergoing internalization by tumor cells.

The claim compositions also can be composed of one or more peptides that are capable of binding an integrin. Integrins are a large family of heterodimeric transmembrane glycoproteins that attach cells to extracellular matrix proteins of the basement membrane or to ligands on other cells. Integrins contain large ($\alpha$) and small ($\beta$) subunits of sizes 120-170 kDa and 90-100 kDa, respectively. Some integrins mediate direct cell to cell recognition and interactions. Integrins contain binding sites for divalent cations $Mg^{2+}$ and $Ca^{2+}$, which are necessary for their adhesive function. Mammalian integrins form several subfamilies sharing common $\beta$ subunits that associate with different a subunits. Integrins are further described in Giancotti et al. (Science, 285(5430): 1028-1033, 1999), the content of which is incorporated by reference herein in its entirety.

An exemplary integrin binding peptide is the Arg-Gly-Asp tripeptide (RGD tripeptide). The RGD tripeptide and its binding to integrins is further described in Ruoslahti et al. (Science, 238(4826):491-497, 1987), the content of which is incorporated by reference herein in its entirety.

In certain embodiments, the fibronectin/integrin binding peptides include two fibronectin binding sites. In certain embodiments, the two binding sites are the same. In other embodiments, the two binding sites are different. The two peptides are joined by an amino acid spacer. According, the compositions of the invention are multivalent, for example, having two fibronectin binding sites as well as an integrin-binding RGD motif. The binding sites may have different specificity (e.g., able to bind to different regions of the same molecule on the surface of tumor cells or to different molecules on the surface of tumor cells and/or to a cross-linking molecule) to induce efficient microclustering and therefore, internalization by tumor cells.

In certain embodiments, the compositions of the invention additionally include a tag on each of the N and C terminal ends of the composition. An exemplary tag is the $His_6$-tag incorporated for the convenience of product purification. FIG. 1 panel A shows an exemplary embodiment of a composition of the invention. The exemplary composition includes two fibronectin binding sites (FBS 1 and FBS2) and one integrin binding peptide, show in FIG. 1 panel A as an Arg-Gly-Asp tripeptide (RGD). The exemplary composition shown in FIG. 1 panel A also shows a $His_6$-tag ($H_6$) on both the N- and C-terminals of the peptide. It will be appreciated by the skilled artisan that the $His_6$-tag is an optional component of the compositions of the invention and is not required. In certain embodiments, the peptide compositions of the invention comprise an amino acid sequence selected from the group consisting of SEQ ID NOs.: 1-4, or a substantial fragment thereof. As shown below, the $His_6$-tags are underlined and two fibronectin binding sequences as well as the RGD sequence are bolded. Amino acids are presented in one-letter or three-letter code according to the following table:

| Full Name | Abbreviation (3 Letter code) | Abbreviation (1 Letter code) |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

It is also to be understood that numerous variations of these exemplary embodiments are contemplated herein. It is to be understood that peptides disclosed herein may be prepared recombinantly, chemically, or by a hybrid method thereof (Berrade, et al., *Cell Mol Life Sci.* 2009, 66: 3909-3922).

(SEQ ID NO.: 1)
MGSSHHHHHHSSGNRQRWFVVWLSTGGNDTR
IVLGRLDQLVPRGSHMASMTGGQQMGRGDFR
SSVDKLAAALEHHHHHH, (SEQ ID NO.: 2)
MGSSHHHHHHSSGNRQRIVLGRLSTGGNDTR
WFVVWLDQLVPRGSHMASMTGGQQMGRGDFR
SSVDKLAAALEHHHHHH, (SEQ ID NO.: 3)
MGSSHHHHHHSSGNRQRIVLGRLSTGGNDTR**I
VLGRLDQLVPRGSHMASMTGGQQMGRGDFRS**
SVDKLAAALEHHHHHH,
and (SEQ ID NO.: 4)
MGSSHHHHHHSSGNRQRWFVVWLSTGGNDTR
WFVVWLDQLVPRGSHMASMTGGQQMGRGDFR
SSVDKLAAALEHHHHHH.

In another embodiment, the peptide composition of the invention comprises an amino acid sequence according to SEQ ID NO: 5, or a substantial fragment thereof, wherein fibronectin binding peptides taken from fibronectin binding proteins from BCG, *Mycobacteria* spp, *Mycoplasma* spp, *Borrelia* spp. are shown in bold. The sequence (H H H H H) of His$_6$-tag is incorporated for the convenience of product purification.

(SEQ ID NO.: 5)
MRKQRWFVVWLGEFGFEWYYQGPGYDQQGY
DQQGLEDLRPKSSLQGIGTHHHHHH.

It will be appreciated by the skilled artisan that the His$_6$-tag is an optional component of the compositions of the invention. In certain embodiments, the peptide compositions of the invention comprise an amino acid sequence selected from the group consisting of SEQ ID NOs.: 6~41 or a substantial fragment thereof.

(SEQ ID NO.: 6)
MGSSHHHHHHSSGNRQRWFVVWLSTGGNDTR
IVLGRLDQLVPRGSHMASMTGGQQMGRGDFR
SSVDKLAAALE, (SEQ ID NO.: 7)
MGSSHHHHHHSSGNRQRIVLGRLSTGGNDTR
WFVVWLDQLVPRGSHMASMTGGQQMGRGDFR
SSVDKLAAALE, (SEQ ID NO.: 8)
MGSSHHHHHHSSGNRQRIVLGRLSTGGNDTR**I
VLGRLDQLVPRGSHMASMTGGQQMGRGDFRS**,
SVDKLAAALE (SEQ ID NO.: 9)
MGSSHHHHHHSSGNRQRWFVVWLSTGGNDTR
WFVVWLDQLVPRGSHMASMTGGQQMGRGDFR
SSVDKLAAALE, (SEQ ID NO.: 10)
MRKQRWFVVWLGEFGFEWYYQGPGYDQQGY
DQQGLEDLRPKSSLQGIGT, (SEQ ID NO.: 11)
SSGNRQRWFVVWLSTGGNDTRIVLGRLDQLVP
RGSHMASMTGGQQMGRGDFRSSVDKLAAALE
HHHHHH, (SEQ ID NO.: 12)
SSGNRQRIVLGRLSTGGNDTRWFVVWLDQLVP
RGSHMASMTGGQQMGRGDFRSSVDKLAAALE
HHHHHH, (SEQ ID NO.: 13)
SSGNRQRIVLGRLSTGGNDTRIVLGRLDQLVP
RGSHMASMTGGQQMGRGDFRSSVDKLAAALE
HHHHHH, (SEQ ID NO.: 14)
SSGNRQRWFVVWLSTGGNDTRWFVVWLDQLV
PRGSHMASMTGGQQMGRGDFRSSVDKLAAAL
EHHHHHH, (SEQ ID NO.: 15)
SSGNRQRWFVVWLSTGGNDTRIVLGRLDQLVP
RGSHMASMTGGQQMGRGDFRSSVDKLAAALE, (SEQ ID NO.: 16)
SSGNRQRIVLGRLSTGGNDTRWFVVWLDQLVP
RGSHMASMTGGQQMGRGDFRSSVDKLAAALE, (SEQ ID NO.: 17)
SSGNRQRIVLGRLSTGGNDTRIVLGRLDQLVP
RGSHMASMTGGQQMGRGDFRSSVDKLAAALE, (SEQ ID NO.: 18)
SSGNRQRWFVVWLSTGGNDTRWFVVWLDQLV
PRGSHMASMTGGQQMGRGDFRSSVDKLAAAL
E, (SEQ ID NO.: 19)
MRKQRWFVVWLGEFGFEWYYQGPGYDQQGY
DQQGLEDLRPKSSLQGIGT, (SEQ ID NO.: 20)
SSGNRQRWFVVWLSTGGNDTRIVLGRLDQLVP
RGSHMASMTGGQQMG, (SEQ ID NO.: 21)
SSGNRQRIVLGRLSTGGNDTRWFVVWLDQLVP
RGSHMASMTGGQQMG, (SEQ ID NO.: 22)
SSGNRQRIVLGRLSTGGNDTRIVLGRLDQLVP
RGSHMASMTGGQQMG, (SEQ ID NO.: 23)
SSGNRQRWFVVWLSTGGNDTRWFVVWLDQLV
PRGSHMASMTGGQQMG,

-continued

SSGNRQRWFVVWLSTGGNDTRIVLGR, (SEQ ID NO.: 24)

SSGNRQRIVLGRLSTGGNDTRWFVVW, (SEQ ID NO.: 25)

SSGNRQRIVLGRLSTGGNDTRIVLGR, (SEQ ID NO.: 26)

SSGNRQRWFVVWLSTGGNDTRWFVVW, (SEQ ID NO.: 27)

RWFVVWLSTGGNDTRIVLGRLDQLVPRGSHM
ASMTGGQQMG, (SEQ ID NO.: 28)

RIVLGRLSTGGNDTRWFVVWLDQLVPRGSHM
ASMTGGQQMG, (SEQ ID NO.: 29)

RIVLGRLSTGGNDTRIVLGRLDQLVPRGSHMA
SMTGGQQMG (SEQ ID NO.: 30)

RWFVVWLSTGGNDTRWFVVWLDQLVPRGSHM
ASMTGGQQMG, (SEQ ID NO.: 31)

RWFVVWLSTGGNDTRIVLGR, (SEQ ID NO.: 32)

RIVLGRLSTGGNDTRWFVVW, (SEQ ID NO.: 33)

RIVLGRLSTGGNDTRIVLGR, (SEQ ID NO.: 34)

RWFVVWLSTGGNDTRWFVVW, (SEQ ID NO.: 35)

RIVLGRLSTGGNDT, (SEQ ID NO.: 36)

LSTGGNDTRWFVVW, (SEQ ID NO.: 37)

RWFVVWLSTGGNDT, (SEQ ID NO.: 38)

LSTGGNDTRIVLGR, (SEQ ID NO.: 39)

RWFVVW,
and (SEQ ID NO.: 40)

RIVLGR. (SEQ ID NO.: 41)

In certain embodiments, a peptide composition comprise a peptide of an amino acid sequence selected from the group consisting of SEQ ID NOs.: 1-41, a combination of any of those sequences, a substantial fragment thereof, or a pharmaceutically acceptable salt thereof. Compositions of the invention are not limited to two fibronectin binding peptide fragments and can include 3, 4, 5, 6, 7, 8, 9, 10, 15, 20, etc. copies of fibronectin binding peptides selected from the group consisting of SEQ ID NOs.: 1~41.

In certain embodiments, the peptide composition comprises a plurality of an amino acid sequence selected from the group consisting of SEQ ID NOs.: 1-41, a combination of any of those sequences, a substantial fragment thereof, or a pharmaceutically acceptable salt thereof.

In certain embodiments, the peptide composition further comprises a cytotoxic agent. In some preferred embodiments, the cytotoxic agent is an anti-cancer agent.

In certain embodiments, the peptide composition further comprises a pharmaceutically acceptable carrier. In some preferred embodiments, the pharmaceutically acceptable carrier is a liposome.

In certain embodiments, the peptide composition further comprises a label for identifying cancer cells wherein cancerous cells express a component that may be bound by fibronectin/integrin binding peptides, wherein the label is coupled to the peptide composition.

In some embodiments, this invention claims a method for targeting or identifying cancer cells wherein cancerous cells express a component that may be bound by fibronectin/integrin binding peptides, the method comprising the step of administering to a subject of a peptide composition comprising a peptide of an amino acid sequence selected from the group consisting of SEQ ID NOs.: 1-41, a combination of any of those sequences, or a substantial fragment thereof, wherein a tracing agent is coupled to the peptide composition.

In some embodiments, this invention claims a method for treating a cancer wherein cancerous cells express a component that may be bound by fibronectin/integrin binding peptides, the method comprising the step of administering to a patient of said cancer therapeutically effective amount of a peptide composition comprising a peptide of an amino acid sequence selected from the group consisting of SEQ ID NOs.: 1-41, a combination of any of those sequences, or a substantial fragment thereof, wherein an anti-cancer agent is coupled to the peptide composition. In some preferred embodiments, the invention is related to a method of treatment for a bladder cancer.

It is to be understood that a pharmaceutical composition disclosed herein may be combined with other components, including, but not limited to, other therapeutically active compounds by the same or different mode of action, and one or more pharmaceutically acceptable carriers, diluents, excipients, and the like.

In some other embodiments, pharmaceutical compositions described herein may contain two or more of the compounds disclosed in this invention.

In another embodiment, it is appreciated herein that the compounds described herein may be used alone or in combination with other compounds useful for treating cancer, including those compounds that may be therapeutically effective by the same or different mode of action.

In some embodiments, disclosed herein is a method for treating a patient with cancer, the method comprising the step of administering a therapeutically effective amount of a pharmaceutical composition comprising a compound disclosed herein to the patient in need of relief from said cancer. It is to be understood that the composition may include other components, including, but not limited to, other therapeutically active compounds by the same or different mode of action, and one or more pharmaceutically acceptable carriers, diluents, excipients, and the like.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantial" or "substantially" can allow for a degree of variability in a value or range, for example, within 90%, within 95%, or within 99% of a stated value or of a stated limit of a range.

A fibronectin/integrin binding peptide or fibronectin/integrin binding peptide fragment is defined as any peptide of SEQ ID NOs. 1~41, a combination of any of those sequences, or a substantial fragment thereof.

A label for identification purpose may be an isotopic label, a radioactive label, a fluorescence label, or the like.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosage may be single or divided, and may be administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

Additionally, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of a compound with other conventional and non-conventional therapeutic treatments, including other anti-tumor agents, radiation therapy, and the like.

The skilled artisan will appreciate that compositions of the invention do not need to have 100% identity with the compositions shown in SEQ ID NOs.: 1~41, and that the invention encompasses compositions having, for example, at least about 40% identity, 45% identity, 50% identity, 55% identity, 60% identity, 65% identity, 70% identity, 75% identity, 80% identity, 85% identity, 90% identity, 95% identity, and 99% identity as compared to SEQ ID NOs.: 1~41. The term "identity" relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) *J. Mol. Biol.* 215:403-410) are available for determining sequence identity.

Furthermore, the skilled artisan will recognize that the compositions shown in SEQ ID NOs.: 1~41 will still function with conserved amino acid substitutions. As used herein an amino acid "substitution" refers to the replacement of one amino acid residue by a different amino acid residue. As used herein, the term "conservative amino acid substitution" is defined herein as exchanges within one of the following five groups:

I. Small aliphatic, nonpolar or slightly polar residues: Ala, Ser, Thr, Pro, Gly;

II. Polar, negatively charged residues and their amides: Asp, Asn, Glu, Gin, cysteic acid and homocysteic acid;

III. Polar, positively charged residues: His, Arg, Lys; Ornithine (Orn);

IV. Large, aliphatic, nonpolar residues: Met, Leu, He, Val, Cys, Norleucine (Nle), homocysteine; and V. Large, aromatic residues: Phe, Tyr, Trp, acetyl phenylalanine.

Compositions of the invention can be formulated with a pharmaceutically acceptable carrier. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In certain embodiments, compositions of the invention are pegylated. As used herein the term "pegylated" and like terms refers to a compound that has been modified from its native state by linking a polyethylene glycol polymer to the compound. As used herein the general term "polyethylene glycol" or "PEG", refers to mixtures of condensation polymers of ethylene oxide and water, in a branched or straight chain, represented by the general formula $H(OCH_2CH_2)_n$ OH, wherein n is at least 9. Absent any further characterization, the term is intended to include polymers of ethylene glycol with an average molecular weight selected from the range of about 500 to about 40,000 Daltons. "Polyethylene glycol" or "PEG" is used in combination with a numeric suffix to indicate the approximate average molecular weight thereof. For example, PEG-5,000 refers to polyethylene glycol having an average molecular weight of about 5,000.

It has been found that compositions of the invention enhance the uptake diagnostic and therapeutic agents by mammalian cells, including for example bladder cells, particularly bladder tumor cells of cancer patients. Particularly, the multivalent nature of the compositions of the invention imparts improved binding affinity and rate of uptake as compared to microcluster compositions. In addition, the compositions of the invention have superior protein solubility/stability as compared to monovalent compositions that are tied together into a microcluster.

Accordingly, the invention also provides methods for treating a cancer in which cancerous cells express a moiety that may be bound by compositions of the invention. The compositions of the invention can be formulated in a pharmaceutically acceptable carrier and administered to the lumen of the bladder using standard techniques known to those skilled in the art. In one embodiment the pharmaceutical composition is delivered by direct administration (via injection or by catheterization) of the composition into the bladder lumen. The pharmaceutical compositions can be further packaged as part of a kit that includes a disposable device for administering the composition to a patient. In one embodiment the kit is provided with a device for administering the composition to a patient. The kit may further include a variety of containers, e.g., vials, tubes, bottles, and the like. The kits will also include instructions for use.

In one embodiment the composition is formulated in association with a liposome, in which claimed peptide composition is presented on the external surface of the liposome and the diagnostic agent or therapeutic agent is encapsulated within the liposome. Since within the bladder, the claimed composition specifically binds to targets only exposed on bladder tumors (normal cells are shielded by the GAG layer), the claimed compositions can be used as an intelligent drug carriers capable of selective delivery of a drug (such as an anti-tumor agent). If a composition of the invention is further linked with a conventional anti-tumor agent, it is possible to increase the efficacy of the anti-tumor agent and significantly reduce side effects adversely affecting normal tissue because the anti-tumor agent is delivered selectively to a bladder tumor cell by the compositions disclosed herein. In accordance with one embodiment the claimed composition/anti-tumor complexes can be further provided with additional cancer targeting moieties (e.g., anti-tumor antibodies) to further target the complexes to cancer cells. In one embodiment the composition is delivered by direct administration (via injection or by catheterization) of the composition into the bladder lumen.

There is no particular limitation in the anti-tumor agent that may be linked with the peptide according to the present invention, and particular examples of such anti-tumor agents include docetaxel, mitoxanthrone, gemcitabine, capecitabine, oxaliplatin, interferon, sunitinib, sorafinib, cis- or carboplatinum, doxorubicin, methotrexate, vincristin, vinorelbine, pemetrexed, gefitinib, etoposid, irinotecan, cyclophosphamide, topotecan, cyclophosphamide, paclitaxel, mitomycin, bevacizumab, trastuzumab, 5-fluorouracil, cetuximab, temozolomide, bevacizumab, procarbacine, cisplatin, adriamycin, vinblastine, busulfan, chlorambucil, cyclophosphamide, melphalan, CCNU, and BCNU. Preferably, the complex can be linked to an anti-tumor agent effective for the treatment of a bladder tumor. Linking of the anti-tumor agent with the complex can be performed by using a conventional method generally known to one skilled in the art, including covalent bonding, crosslinking, etc.

In addition, the composition according to the present invention may further comprise pharmaceutically acceptable carriers that are added conventionally to a general pharmaceutical composition. In the case of injection formulation, particular examples of the pharmaceutically acceptable carriers include a buffering agent, a preserving agent, an anesthetic agent, a solubilizing agent, an isotonic agent and a stabilizer. The composition can as a unit dose ample or a multidose vial.

A "liposome" as used herein refers to a small, spherical vesicle composed of lipids, particularly vesicle-forming lipids capable of spontaneously arranging into lipid bilayer structures in water with its hydrophobic moiety in contact with the interior, hydrophobic region of the bilayer membrane, and its head group moiety oriented toward the exterior, polar surface of the membrane. Vesicle-forming lipids have typically two hydrocarbon chains, particularly acyl chains, and a head group, either polar or nonpolar. Vesicle-forming lipids are either composed of naturally-occurring lipids or of synthetic origin, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids for use in the composition of the present invention include glycolipids and sterols such as cholesterol and its various analogs which can also be used in the liposomes.

Cationic lipids, which typically have a lipophilic moiety, such as a sterol, an acyl or diacyl chain, and where the lipid has an overall net positive charge can also be suitably used in liposomes. The head group of the lipid typically carries the positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethyl-ammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethyl-ammonium chloride (DOTMA); 3 [N~(N',N'-dimethylaminoethane) carbamolyjcholesterol (DC-Choi); and dimethyldioctadecylammonium (DDAB). The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids.

The liposomes can include a vesicle-forming lipid derivatized with a hydrophilic polymer to form a surface coating of hydrophilic polymer chains on the liposomes surface. A vesicle-forming lipid, in particular a phospholipid, such as distearoyl phosphatidylethanolamine (DSPE), may be covalently attached to a hydrophilic polymer, which forms a surface coating of hydrophilic polymer chains around the liposome. Hydrophilic polymers suitable for derivatization with a vesicle-forming lipid include polyvinylpyrrolidone, polyvmylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyemylcellulose, polyethyleneglycol, polyaspartamide and hydrophilic peptide sequences. The polymers may be employed as homopolymers or as block or random copolymers.

One hydrophilic polymer chain suitable for use is polyethyleneglycol (PEG), preferably as a PEG chain having a molecular weight between 200-20,000 daltons, or between 500-10,000 daltons, or between 750-5000 daltons. Methoxy or ethoxy-capped analogues of PEG are also preferred hydrophilic polymers, commercially available in a variety of polymer sizes, e.g., 120-20,000 Daltons. In one embodiment the PEG polymers are derivatized (e.g. at the free end) to further comprise a ligand that binds to a fibronectin/integrin binding peptides.

Preparation of Vesicle-Forming Lipids Derivatized with Hydrophilic Polymers has been described, for example in U.S. Pat. Nos. 5,395,619, 5,013,556, 5,631,018 and in WO 98/07409. It will be appreciated that the hydrophilic polymer may be stably coupled to the lipid, or coupled through an unstable linkage, which allows the coated liposomes to shed the coating of polymer chains as they circulate in the bloodstream or in response to a stimulus. In one embodiment the liposomes are derivatized to include a plurality of antibodies or ligands that specifically bind to a fibronectin/integrin binding peptides.

Incorporation By Reference References and citations to other documents, such as patents, patent applications, patent publications, journals, books, papers, web contents, have been made throughout this disclosure. All such documents are hereby incorporated herein by reference in their entirety for all purposes.

Equivalents Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein. It is to be understood that peptides disclosed herein may be prepared recombinantly, chemically, or by a combination method thereof (Berrade, et al., *Cell Mol Life Sci.* 2009, 66: 3909-3922).

Peptide Composition Preparation. Bacterially produced recombinant peptide were generated in Rosetta cells (Novagen) by inducing expression of pET28 plasmids with 0.05 mM IPTG for 5 h at 30° C. Peptides were purified in PBS, 0.1% Tween, and 15% glycerol using $Ni^{2+}$NTA resin (Novagen) according to standard protocols of the vendor and eluted with PBS containing 250 mM imidazole for 2-8 h at 4° C. The eluate is then desalted with Pierce Zeba Spin columns into PBS. The purified protein concentration was measured using Precision Red protein assay reagent (Cytoskeleton).

Alternatively, all peptides of the present invention can be synthesized by solid-phase synthesis or solution phase synthesis, or a combination of both, with peptide chain assembly on solid phase and cyclization or other modifications on resin or in solution. Such methods are well known in the art (see W. C. Chan and P D. White, *Fmoc Solid Phase Peptide Synthesis, A Practical Approach*, Oxford University Press, 2000, and references cited therein).

EXAMPLE 1: Compositions of the Invention Co-Localize with Fibronectin

T24 human bladder tumor cells grown on coverslips for 24 h were incubated with compositions of the invention, washed, fixed and immunostained with anti-His6 (red) and anti-FBN (green) antibodies. FIG. 1 panel B is a set of slides showing that compositions of the invention co-localize with fibronectin. Arrows point some areas of colocalization. Scale bar: 20 microns.

EXAMPLE 2: Internalization of the Compositions of the Invention

T24 cells expressing GFP-tagged constitutively activated Rab5 (Q79L) mutant were grown on coverslips. This Rab5 variant leads to the formation of easy to visualize giant GFP-labeled endosomes. T24 cells were incubated with compositions of the invention, fixed and immunostained with anti-His6 antibody. FIG. 1 panel C is a set of slides showing signals from compositions of the invention located inside GFP-positive structures, meaning that compositions of the invention were internalized by the tumor cells. Arrows point to some to internalized composition signals. Scale bar: 20 microns.

Example 3: Compositions of the Invention Promote Nanoparticle Uptake

GFP-Rab5Q79L expressing cells were incubated with fluorescent nanoparticles decorated with compositions of the invention. As shown in FIG. 1 panel D, internalized compositions of the invention were detected as signal detected inside of GFP-labeled structures (Arrows). Scale bar: 10 microns. The detailed experimental procedure has been described by Coon et al., *Int. J. Cancer:* 131(3), 591-600 (2012).

To summarize, the compositions of the invention co-localized with cell-associated fibronectin (FIG. 1 panel B), owning to the structural design of the multivalent construct, the presence of an RGD motif and two FBS. In addition, multivalency gives self-clustering properties to the compositions of the invention and, as indicated above, it leads to fast composition uptake (FIG. 1 panel C). In fact, compositions of the invention disclosed herein were competent to promote nanoparticle uptake (FIG. panel D) and, as opposed to monovalent ligands, do not need to be present in multiple units to confer multivalency/micro-clustering properties to a nanoparticle, and could be used at nanomolar concentrations without compromising the efficacy.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that the scope of the present methods and composition matters be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A peptide composition comprising a peptide of an amino acid sequence selected from the group consisting of SEQ ID NOs: 1-39, a combination of any of those sequences, or a pharmaceutically acceptable salt thereof.

2. The peptide composition according to claim 1, wherein the peptide comprises a plurality of an amino acid sequence selected from the group consisting of SEQ ID NOs: 1-39, a combination of any of those sequences, or a pharmaceutically acceptable salt thereof.

3. The peptide composition according to claim 1, further comprising a cytotoxic agent.

4. The peptide composition according to claim 3, wherein the cytotoxic agent is an anti-cancer agent.

5. The peptide composition according to claim 1, wherein the composition further comprises a pharmaceutically acceptable carrier.

6. The peptide composition according to claim 5, wherein the pharmaceutically acceptable carrier is a liposome.

7. A method for targeting or identifying cancer cells wherein cancerous cells express a component that may be bound by fibronectin/integrin binding peptides, the method comprising the step of administering to a subject of a peptide composition according to claim 1, wherein a label for identification is coupled to the peptide composition.

8. A method for targeting or identifying cancer cells wherein cancerous cells express a component that may be bound by fibronectin/integrin binding peptides, the method comprising the step of administering to a subject of a peptide composition comprising a peptide of an amino acid sequence selected from the group consisting of SEQ ID NOs: 1-39, and a combination of any of those sequences, wherein a label for identification is coupled to the peptide composition.

9. A method for treating a cancer wherein cancerous cells express a component that may be bound by fibronectin/integrin binding peptides, the method comprising the step of administering to a patient of said cancer therapeutically effective amount of a peptide composition according to claim 1, wherein an anti-cancer agent is coupled to the peptide composition.

10. The method according to claim 9, wherein the cancer is a bladder cancer.

11. The method according to claim 9, further comprising the step of administrating a therapeutically effective amount of another anti-cancer agent to the patient of said cancer.

12. (Withdrawn, Currently Amended) A method for treating a cancer wherein cancerous cells express a component that may be bound by fibronectin/integrin binding peptides, the method comprising the step of administering to a patient of said cancer therapeutically effective amount of a peptide composition comprising a peptide of an amino acid sequence selected from the group consisting of SEQ ID NOs: 1-39, and a combination of any of those sequences, wherein an anti-cancer agent is coupled to the peptide composition.

13. The method according to claim 12, wherein the cancer is a bladder cancer.

14. The method according to claim 12, further comprising the step of administrating a therapeutically effective amount of another anti-cancer agent to the patient of said cancer.

* * * * *